(12) United States Patent
Clements et al.

(10) Patent No.: US 6,498,278 B1
(45) Date of Patent: Dec. 24, 2002

(54) ALKOXYLATION OF 6-MEMBERED ALKYLENE CARBONATES

(75) Inventors: John H. Clements, Round Rock, TX (US); Howard P. Klein, Austin, TX (US); Edward T. Marquis, Austin, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/946,312

(22) Filed: Sep. 5, 2001

(51) Int. Cl.7 .......................... C07C 41/00; C07C 43/16
(52) U.S. Cl. ....................... 568/630; 568/648
(58) Field of Search ................... 568/630, 648

(56) References Cited

U.S. PATENT DOCUMENTS

| | | | |
|---|---|---|---|
| 4,261,922 A | 4/1981 | Kem | 260/512 R |
| 4,310,707 A | 1/1982 | Strege | 568/648 |
| 4,341,905 A | 7/1982 | Strege | 568/45 |
| 4,474,951 A | 10/1984 | Pope | 536/95 |
| 5,059,723 A | 10/1991 | Dressler | 568/45 |
| 5,104,987 A | 4/1992 | King | 544/401 |
| 5,679,871 A | 10/1997 | Nava | 568/648 |
| 6,046,326 A | 4/2000 | Lavalee | 544/221 |
| 6,063,827 A | 5/2000 | Sacripante et al. | 522/6 |

*Primary Examiner*—Deborah O. Lambkin
(74) *Attorney, Agent, or Firm*—Russ R. Stolle; Ron D. Brown; Christopher J. Whewell

(57) ABSTRACT

A method for the preparation of γ-hydroxy ethers from cyclic organic carbonates and active-hydrogen-containing compounds in one form includes the steps of contacting an active-hydrogen-containing compound and a cyclic organic carbonate compound containing a six-membered ring, and a catalyst, running the reaction at a suitable temperature, and isolating the γ-hydroxy ether as a mixture that can be purified or used directly as produced in the reaction.

22 Claims, No Drawings

ALKOXYLATION OF 6-MEMBERED ALKYLENE CARBONATES

FIELD OF THE INVENTION

The present invention relates generally to a process for the preparation of hydroxyalkyl ether compounds. More particularly, the present invention is concerned with the preparation of γ-hydroxy ether compounds by reacting species having active hydrogen atoms with organic carbonates containing six-membered rings.

BACKGROUND OF THE INVENTION

Methods exist for the alkoxylation of organic carbonates such as ethylene carbonate and propylene carbonate by reacting them with certain organic compounds including phenols and alcohols to produce β-hydroxy ethers.

β-Hydroxy ethers are currently widely used in a number of different applications. γ-Hydroxy ethers may be used in place of β-hydroxy ethers as functional fluids or as spacers in the synthesis of urethane and/or ester containing polymer formulations.

The methods used to prepare β-hydroxy ethers typically do not provide for satisfactory synthesis of γ-hydroxy ethers, giving unacceptably low yields. Therefore, there is a need for a process by which γ-hydroxy ethers may be readily prepared.

SUMMARY OF THE INVENTION

The present invention provides a method for the preparation of γ-hydroxy ethers from cyclic organic carbonates and active-hydrogen-containing compounds.

The method of the present invention includes the steps of contacting an active-hydrogen-containing compound, a cyclic organic carbonate compound containing a six-membered ring, and a catalyst.

The reaction is run at a suitable temperature, and the γ-hydroxy may be isolated as a mixture that can be purified or used directly as produced in the reaction.

DETAILED DESCRIPTION OF THE INVENTION

The present invention is a process that includes providing a hydroxylated or thiolated aromatic compound (containing an "active-hydrogen species"), a cyclic organic carbonate containing a six-membered ring, and a catalyst; and reacting the active-hydrogen species and the cyclic organic carbonate in the presence of the catalyst to form an alkoxylated compound as depicted below

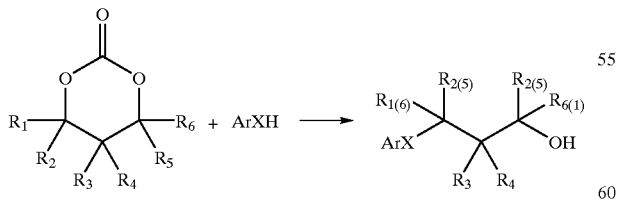

where $R_1$ through $R_6$ are each independently hydrogen or a linear or branched alkyl group, Ar is an aryl group, and X is oxygen, sulfur, or nitrogen.

The active-hydrogen species that may be employed are numerous and known in the art. The term "active-hydrogen species" in this application means any compound with a sufficiently acidic hydrogen atom to under go the reaction depicted above. These include, but are not limited to, both mono- and polyhydric phenols and thiophenols, phenolic resins, aniline, cyanuric acid.

Examples of monohydric phenols which may be employed generally include phenol, β-naphthol; p,p'-sec-butylidenediphenol; o-chlorophenol; o-cresol; p-propyl phenol; p-bis(o-cresol); phenyl phenol; nonyl phenol; mono-; di-; and tri-alkyl phenols; $C_1$ to $C_{18}$ substituted phenols, such as nonylphenol; polyaralkylphenols; halophenols; arylphenols; naphthols; and hydroxyquinoline.

Examples of some useful di- and polyhydric hydroxyl compounds include Bisphenol A; cyanuric acid; catechol; resorcinol; hydroquinone; 4,4'-biphenol; 4,4'-isopropylidenebis(o-cresol); 4,4'-isopropylidenebis(2-phenylphenol); alkylidenediphenols such as bisphenol A, pyrogallol, and phloroglucinol; naphthalenediols; phenol/formaldehyde resins; resorcinol/formaldehyde resins; and phenol/resorcinol/formaldehyde resins.

Exemplary thiophenols include thiophenol; o-thiocresol; m-thiocresol; p-thiocresol; 4,4'-thiodiphenol; and 4,4'-thiobisbenzenethiol. Alkaline salts of phenols may also be used. Mixtures of any of the above compounds may be employed in the process. The phenol or thiophenol compound may be employed in any suitable amount in the process.

Numerous cyclic organic carbonate compounds may be used in the invention. In general, suitable organic carbonate compounds include any cyclic carbonate having a six-membered ring that is capable of undergoing alkoxylation with an aromatic compound containing an active-hydrogen. Generally, compounds of the formula

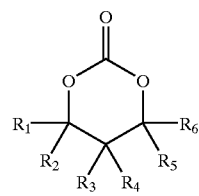

where $R_1$ through $R_6$ may each independently be hydrogen, or linear or branched alkyl containing from one to six carbons atoms. A preferred configuration is for at least four of the substituents to be hydrogen, and for one of the remaining two substituents to be either methyl or ethyl. Particularly suitable cyclic organic carbonates are any substituted 1,3-dioxan-2-one, such as the 4-, and 5-methyl derivatives (I and II respectively).

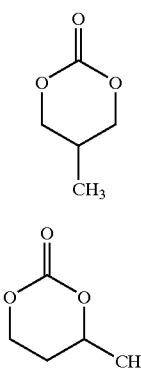

I

II

The catalyst employed in the alkoxylation reaction may be selected from an alkali metal; an alcohol-derived salt of the alkali metal; alkali metal carbonates; stannates; tertiary amines; quaternary ammonium salts; phosphonium salts; and mixtures of any of these, or any other material capable of catalyzing the reaction.

Nonlimiting examples of specific catalysts include potassium iodide and hydroxide; potassium carbonate; potassium stannate; potassium metal; sodium metal; potassium t-butoxide; triphenylphosphine; tributylphosphine; diphenylbutylphosphine; dibutylphosphine; tetraphenylphosphonium bromide; triphenyl phosphonium acetate; tetrabutylphosphonium bromide; tetrabutylphosphonium acetate; 2-methylimidazole; N-(2'-hydroxyethyl)-2-methylimidazole; piperidine; triethylamine, tributylamine; zinc octoate; magnesium octoate; zirconium hexanoate; dimethyl cyclohexylamine; triethylamine; zinc acetate; and benzotriazole.

The catalyst may be used in various amounts in the process. Typically as is known to one skilled in the art, the preferred amount will vary depending on the type of active-hydrogen species, cyclic organic carbonate, and particular catalyst used. Reaction conditions such as temperature and pressure also may also influence the optimum quantity of catalyst needed. The amount of catalyst is generally any amount between about 0.005 and 3.0 percent by weight based on the total quantity of reaction components. The preferred amount of catalyst is any value between about 0.01 to 1.0 percent by weight.

Additional components that are known to those of skill in the art may be utilized in the process. As an example, the reaction may take place in the presence of an appropriate inert solvent such as, for example, tetrahydronaphthalene; naphthalene; anisole; dimethyl formamide; diethyleneglycol dimethylether (diglyme) and triethyleneglycol dimethylether (triglyme).

The use of a solvent will typically depend on its properties and on the types of active-hydrogen species, cyclic organic carbonate, and catalyst used. Typically, the addition of a solvent is not necessary for carrying out the reaction. Hydroquinone may also be added to the reaction mixture to inhibit polymerization of the cyclic carbonate.

The process may be carried out using various molar ratios of the cyclic organic carbonate compound to the active-hydrogen species. Preferably, the cyclic organic carbonate may be added in excess ranging from about 1.02 to 1.50 moles per every mole of hydroxyl or thiol group present in the active-hydrogen species. More preferably, the excess of cyclic carbonate will be between about 1.05 to 1.25 mole for every mole of hydroxy or thiol group present in the active-hydrogen moieties. In the event that an excess of cyclic organic carbonate compound is used, the amount present after the reaction may optionally be removed by vacuum distillation or other appropriate purification procedure.

The process of the invention may be carried out in any suitable vessel that is constructed to contain the reactants and products. Preferably, the materials of the vessel are inert under the conditions employed during the process. Such materials may include glass, stainless steel, and the like.

The reaction may be run at any suitable temperature, preferably from about 100° C. to 220° C., and more preferably from about 150° C. to 200° C. It is believed that the reaction rate of the alkoxylation reaction is temperature dependent, with faster rates being observed at higher temperatures, and the decomposition of reactants and products likely to occur at higher temperatures. The heating of the reaction vessel to the operating temperature may be achieved by any suitable means such as a heat lamp, heating mantle, oil bath, and the like.

The reaction time to obtain adequate conversion of the active-hydrogen species will typically vary depending on various factors such as, for example, temperature, catalyst type, type of active-hydrogen species and cyclic organic carbonate. Generally, the time that is sufficient for the reaction to take place is from about 5 and 12 hours.

Additional means may be employed to facilitate the reaction of the active-hydrogen species and the cyclic organic carbonate. For example, the reaction may proceed with or without stirring by mechanical, magnetic or other known means. In addition, to avoid liquid entrapment during the evolution of carbon dioxide during the reaction, it is preferred to employ a suitable condenser. The alkoxylated compounds produced in accordance with the invention may be used as is, or may be purified by any of well-known techniques, including fractional distillation or crystallization.

The following examples are demonstrative of specific embodiments of the present invention. They are in no way intended to limit the scope of the subject matter of the present invention in any manner.

EXAMPLE 1

123.8 G of 5-methyl-1,3-dioxan-2-one (1.066 moles prepared by transesterification of 2-methyl-1,3-propanediol with diethyl carbonate), 98.7 g of phenol (1.049 moles), and 1.20 g of tetrabutylphosphonium bromide catalyst (0.54 weight %) were charged to a one liter round-bottom flask equipped with a thermocouple probe, overhead stirrer, and a condenser. 0.66 g of hydroquinone was added to the mixture to prevent the thermally initiated polymerization of the cyclic carbonate.

The system was purged with nitrogen for 30 minutes, and heated slowly to 160° C. At 160° C. the reaction mixture had an orange color, and the slow evolution of carbon dioxide was observed. The temperature was gradually increased to 190° C. over a period of 1.5 hours, and held at that temperature for three hours, at which time the evolution of gas had ceased. The resulting orange liquid was cooled and analyzed by liquid chromatography-mass spectroscopy. The analysis showed 33.5% phenoxy-2-methyl-3-propanol, 16.5% phenol, 13.8% dialkoxylation product, 6.25% 5-methyl-1,3-dioxan-2-one, 8.3% 3-butenol, 3.8% esterification product, 3.2% 2-methyl-2-propenol, and 14.7% of unidentified material, for a total isolated yield of 36%

EXAMPLE 2

92.26 g of 4-methyl-1,3-dioxan-2-one (0.794 moles prepared by transesterification of 1,3-butanediol with diethylcarbonate), 69.8 g of phenol (0.742 moles), and 1.11 g tetrabutylphosphonium bromide catalyst (0.68 weight %) were charged to a one liter round-bottom flask equipped with a thermocouple probe, overhead stirrer, and condenser. 0.51 g of hydroquinone was added to the mixture to prevent the thermal polymerization of the cyclic carbonate.

The system was purged with nitrogen for 30 minutes, and heated slowly to 160° C. At 160° C. the reaction mixture had an orange color, and the slow evolution of carbon dioxide was observed. The temperature was gradually increased to 190° C. over a period of 1.5 hours, and held at that temperature for two hours, at which time the evolution of gas had ceased. The resulting orange liquid was cooled and analyzed by liquid chromatography-mass spectroscopy. The analysis showed 45.4% phenoxy-methyl-3-propanol (mixture of two isomers), 10.6% esterification product, 10.5% phenol, 4.4% dialkoxylation product, 3.6% 1,3- butanediol, 3.0% di (3-butanol)carbonate, 2.6% 4-methyl-1,3-dioxan-2-one, and 19.1% unidentified material for a total isolated yield of 41%.

EXAMPLE 3

108.7 g of 5-butyl-5-ethyl-1,3-dioxan-2-one (0.584 mol., prep'd by transesterification of 2-butyl-2-ethyl-1,3-propanediol with diethyl carbonate). 54.7 g of phenol (0.58 mol), and 0.82 g tetrabutylphosphonium bromide (0.50 wt. %) were charged to a one-liter round-bottom flask equipped with a thermocouple probe, overhead stirrer, and condenser. The system was purged with nitrogen for 35 minutes, and heated slowly to 200° C. The slow evolution of carbon dioxide was first observed when the temperature of the mixture reached 190° C. After 9 hours at 200° C., the mixture was cooled. The resulting pale yellow, viscous liquid obtained was analyzed by gas chromatography-mass spectrometry. The analysis showed the mixture to comprise 15.5% phenoxy-2-butyl-2-ethyl-3-propanol, 14.3% phenol, 36.4% 5-butyl-5-ethyl-1,3-dioxan-2-one, 7.6% 2-butyl-2-ethyl-1,3-propanediol, and 22.6% unidentified species for a total isolated yield of 15.5%.

What is claimed:

1. A method of alkoxylation comprising the steps of:
    a) contacting an active-hydrogen-containing species with a cyclic organic carbonate compound containing a six-membered ring, in the presence of a catalyst; and
    b) recovering the alkoxylated compound formed.

2. The method recited in claim 1 wherein the active-hydrogen-containing species is an aromatic hydroxy or thiol compound.

3. The method recited in 2 wherein the aromatic hydroxy or thiol compound is selected from a group consisting of phenol, bisphenol A, and thiophenol.

4. The method recited in claim 1, wherein the active-hydrogen-containing species comprises a monohydric phenol selected from the group consisting of β-naphthol; p,p'-sec-butylidenediphenol; o-chloro phenol; o-cresol; p-propyl phenol; p-bis(o-cresol); phenyl phenol; nonyl phenol; mono-; di-; and tri-alkyl phenols; $C_1$ to $C_{18}$ substituted phenols; polyaralkylphenols; halophenols; arylphenols; naphthols, and hydroxyquinoline.

5. The method recited in claim 1, wherein the active-hydrogen-containing species comprises a di- or polyhydric hydroxyl compound chosen from the group consisting of Bisphenol A; cyanuric acid; catechol; resorcinol; hydroquinone; 4,4'-biphenol; 4,4'-isopropylidenebis(o-cresol); 4,4'-isopropylidenebis(2-phenyl phenol); alkylidenediphenols; naphthalenediols; phenol/formaldehyde resins; resorcinol/formaldehyde resins; and phenol/resorcinol/formaldehyde resins.

6. The method recited in claim 1, wherein the active-hydrogen-containing compound comprises a thiophenol chosen from the group consisting of thiophenol; o-thiocresol; m-thiocresol; p-thiocresol; 4,4'-thiodiphenol; and 4,4'-thiobisbenzenethiol; alkaline salts of any of the above mentioned compounds, and mixtures of any of the above compounds.

7. The method recited in claim 1 wherein the reaction is carried out at any temperature in the range of about 100° C. to about 210° C.

8. The method recited in claim 1, wherein the reaction is carried out at any temperature in the range of about 160° C. to about 190° C.

9. The method recited in claim 1 wherein the quantity of catalyst present based on total reactant weight is from about 0.05 to about 10 weight percent.

10. The method recited in claim 1, wherein the catalyst comprises tetrabutylphosphonium bromide.

11. The method recited in claim 1, wherein the catalyst is chosen from the group consisting of potassium iodide; potassium hydroxide; potassium carbonate; $K_2SnO_3$; potassium metal; sodium metal; potassium t-butoxide; triphenylphosphine; tributylphosphine; diphenylbutylphosphine; triphenylphosphonium bromide; triphenyl phosphonium acetate; tributylphosphonium bromide; tributylphosphonium acetate; imidazole; 2-methylimidazole; N-(2'-hydroxyethyl)-2-methylimidazole; piperidine; morpholine; triethylamine; triethyl amine; tributyl amine; zinc octoate; magnesium octoate and zirconium hexanoate.

12. The method recited in claim 1, wherein the carbonate comprises the general formula

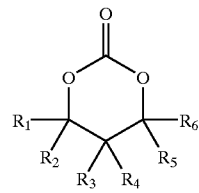

wherein $R_1$ through $R_6$ are each independently hydrogen, or linear or branched alkyl groups containing from one to six carbons atoms.

13. The method recited in 1 wherein the cyclic organic carbonate compound is 5-methyl-1,3-dioxa-2-one.

14. The method recited in claim 1 wherein the cyclic organic carbonate compound is 4-methyl-1,3-dioxa-2one.

15. The method recited in claim 1, wherein the step of contacting is done in the presence of a solvent.

16. The method recited in claim 15, wherein the solvent is selected from the group consisting of toluene; xylene; cyclohexane; tetrahydronaphthalene; naphthalene, anisole, and chlorobenzene.

17. The method recited in claim 1, wherein the step of contacting is done in the presence of an effective amount of hydroquinone to inhibit polymerization of the cyclic organic carbonate.

18. The process recited in claim 1, wherein the recovering step includes a method selected from the group consisting of distillation, decantation, fractional crystallization, and solvent extraction.

19. The process recited in claim 1, wherein the alkoxylation product is a γ-hydroxy ether.

20. A reaction product mixture comprising:
    a) a γ-hydroxy ether;
    b) a carbonate ester; and
    c) an active-hydrogen containing compound;
    wherein the γ-hydroxy ether comprises at least about 4 percent by weight of the total weight of the reaction product mixture.

21. The reaction product mixture recited in claim 20, wherein the carbonate ester comprises at least about 10 weight percent of the total weight of the reaction product mixture.

22. The reaction product mixture recited in claim 20, wherein the active-hydrogen compound comprises at least about 30 weight percent of the total weight of the reaction product mixture.

* * * * *